United States Patent
Fleischer

(10) Patent No.: US 7,045,099 B2
(45) Date of Patent: *May 16, 2006

(54) METHOD FOR THE TREATMENT OF AIR OF AT LEAST ONE ROOM BY AIR IONIZATION

(75) Inventor: Werner Fleischer, Schwarzenberg (CH)

(73) Assignee: Lk Luftqualität AG, Reissbühl (CH)

( * ) Notice: Subject to any disclaimer, the term of this patent is extended or adjusted under 35 U.S.C. 154(b) by 545 days.

This patent is subject to a terminal disclaimer.

(21) Appl. No.: 10/248,231

(22) Filed: Dec. 30, 2002

(65) Prior Publication Data

US 2003/0086813 A1 May 8, 2003

Related U.S. Application Data

(63) Continuation-in-part of application No. 09/788,287, filed on Feb. 16, 2001, now Pat. No. 6,528,023.

(30) Foreign Application Priority Data

Feb. 18, 2000 (DE) .................. 100 07 523

(51) Int. Cl.
*B01D 19/08* (2006.01)

(52) U.S. Cl. .................. 422/121; 422/22; 204/164

(58) Field of Classification Search ................ 422/121, 422/22; 204/164
See application file for complete search history.

(56) References Cited

U.S. PATENT DOCUMENTS 6,528,023 B1 * 3/2003 Fleischer ............... 422/186.04

* cited by examiner

*Primary Examiner*—Kishor Mayekar
(74) *Attorney, Agent, or Firm*—Gudrun E. Huckett

(57) ABSTRACT

In a treatment method of room air by air ionization, sensors such as air-quality sensors, an airflow sensor, an air humidity sensor, an ozone sensor, are provided. Parameters such as oxidizable air components, relative humidity, flow velocity, flow volume, ozone level, and intensity of oxygen ions are measured. The level of ionization power of the ionization apparatus is determined by an electronic control device based on the measured parameters. The ionization power is lowered, when a predetermined ozone value is detected, and, when the ozone level continues to increase after lowering the ionization power indicating an external ozone source, ozone decomposition is initiated by changing a time period of the applied periodic alternating voltage, supplied in the form of alternating pulses or packages of alternating pulses of a preset number or a combination of alternating pulses and packages of alternating pulses of a preset number.

7 Claims, 2 Drawing Sheets

METHOD FOR THE TREATMENT OF AIR OF AT LEAST ONE ROOM BY AIR IONIZATION

CROSS REFERENCE TO RELATED APPLICATIONS

This application is a continuation-in-part of U.S. application Ser. No. 09/788,287, now U.S. Pat. No. 6,528,023 B2, filed Feb. 16, 2001.

BACKGROUND OF INVENTION

1. Field of the Invention

The invention relates to methods and devices for the treatment of air of at least one room by air ionization wherein this ionization is realized by electrical discharge in ionization tubes or in corona discharge tubes.

2. Description of the Related Art

It is known that the room air and thus the breathing air can be treated with ionization apparatus. In this context, bacteria and other germs are killed and large molecules are split up into smaller molecule fragments. Complex and large molecules are, inter alia, odor-causing substances so that odor can be suppressed by means of air ionization. Moreover, it is even possible to eliminate room air loading situations which are detrimental to the health of persons in the room as well as to effectively reduce microorganisms in the air.

In ionization apparatus a high electrical field between two voltage potentials is used. For this purpose, as is known in the art, ionization tubes in the form of glass tubes are used in which the inner side is coaxially coated and the outer side is electrically conducting. When a sufficiently high electrical voltage is supplied, the glass of the wall forms a dielectric substance in which a large electrical field is present. The air flowing through is then enriched with ions. An important disadvantage is that starting at a certain voltage ozone is formed, and the ozone formation increases with increasing voltage.

In German patent document 43 34 956.0 C2 a method for the treatment of air with ions and a device for performing the method are described wherein the long-term stability of the ionization apparatus is increased. The discharge voltage is controlled such that the threshold for an increased ozone generation is never surpassed. As in the case of unloaded natural air, with the prior art method and the prior art device a minimum intensity of oxygen ions of approximately 5% as the lower process limit is technically maintained, and this corresponds substantially to the natural value. By means of the employed sensors, which are provided in the form of air-quality sensors, an airflow sensor, and an air humidity sensor, this minimum intensity within a load range can be substantially maintained.

When outer disturbance sources are present, i.e., an increased ozone loading in the ambient air, for example, in smog situations resulting from sun radiation, different situations in nature, for example, inverted weather situations, thunderstorms, outer energy fields, or in the case of inner disturbance sources, for example, in the form of electrical devices installed in the vicinity of air supply lines for transformation of voltage or frequencies, electromagnetic radiation, or other radiation, the loading with ozone in the supply air can increase undesirably and can lead to surpassing the limit value.

SUMMARY OF INVENTION

It is an object of the present invention to provide a method and a device for performing the method of the aforementioned kind such that a loading with ozone will not surpass a certain limit value.

In accordance with the present invention, this is achieved with respect to the method in that air ionization is carried out by means of electrical discharge in ionization tubes or in corona discharge tubes, wherein the level of ionization power is determined by an electronic control device as a function of the parameters:
  oxidizable air components in the air to be treated,
  relative air humidity in the air to be treated,
  flow velocity or volume flow of the air to be treated,
  ozone loading in the supplied air, and
  minimum intensity of oxygen ions, determined by sensors, i.e., a first air quality sensor, an airflow sensor, an air humidity sensor, an ozone sensor, and/or a second air-quality sensor.

In accordance with the present invention, this is achieved with respect to the device for performing the method according to the invention, wherein a supply line for supplying treated air is connected to at least one room to be supplied with treated air, in that a second air-quality sensor is provided in the room and/or in an exhaust line of the room and/or in the circulation line of the room between an exhaust line and the air treatment device, and in that the supply line between the air treatment device and the at least one room is provided with at least one ionization apparatus, an airflow sensor, and air humidity sensor, and an ozone sensor, and that the air-quality sensors, the airflow sensor, the air humidity sensor, and the ozone sensor are functionally connected via signal lines with the electronic control device.

The methods and devices for air treatment of at least one room by ionization, carried out by electrical discharge in ionization tubes or by corona discharge, are characterized, in particular, in that the level of ionization power is determined by an electronic control device depending on the values or parameters of the oxidizable air components (for example, vaporous organic compounds—VOC), the relative humidity, the flow velocity/volume flow, the loading of the air to be treated by ozone, while ensuring a minimum intensity of positive and negative oxygen irons (matching the natural state of the air), which parameters or values are determined by sensors, i.e., a first air-quality sensor, an airflow sensor, and air humidity sensor, an ozone sensor and/or a second air-quality sensor.

The method according to the invention is controlled such that, in particular, the following values are determined directly: loading of the external air with volatile hydrocarbons by a first air quality sensor, the flow velocity or the volume flow of the air to be treated by an airflow sensor, the relative humidity of the air to be treated by an air humidity sensor, the contents of ozone in the supply air by an ozone sensor, and the oxidizable air components of the exhaust air and/or of the circulating air by means of a second air quality sensor in the circulation line between the room and the air treatment device or, optionally, in the exhaust line or, optionally, in the room. Corresponding to the above listed measurement values, the level of the ionization power of at least one or more ionization apparatus is controlled by the electronic control device such that the minimum intensity of oxygen ions is lowered and, when ozone values are too high, the ozone is reduced by formation of free radicals as well as natural oxygen clusters.

The special advantage resides in that, in particular, also the value of ozone in the supply air is correspondingly evaluated, controlled, and, when reaching or surpassing fixed points, signals are sent to the electronic control device. Accordingly, the ionization apparatus is affected such that a detrimental effect on persons present in the room is prevented as much as possible. This is the result of the ozone sensor provided in the supply line of the room and connected via the electronic control device to the ionization apparatus.

The electronic control device ensures an indeed stable supply air ionization which corresponds to natural levels wherein a predetermined ozone limit value is not surpassed and wherein, in extreme situations, ozone is eliminated. In this connection, the above indicated sensor signals are evaluated and processed in the control device such that optimized alternating pulses, which are supplied to the at least one ionization apparatus, automatically adjust a situation-specific ionization intensity. Each alternating pulse is a full sine curve which can be cut off when passing through zero, if needed. The frequency and voltage (potential) are not changed in this connection. Advantageously, in contrast to prior art solutions, several alternating pulses (several sine curves) are combined to packages or sets. The package size and thus the number of the alternating pulses of each package or set provides a possibility to further optimize the air ionization and to minimize at the same time loading of the electrical power mains. It is important in this connection that the discharge voltage remains constant so that a stable air ionization is ensured.

The solution according to the invention is characterized furthermore by ensuring a process safety and an increase of efficiency wherein also the safe application of air- technological devices with a directed use of air circulation is provided. In this connection, for high external temperatures in summer and low temperatures in winter, considerable energy savings for cooling or heating are realized. Further advantageous effects can be derived from reconstruction of already existing and the design of new air-technological devices. These are, inter alia, lowering of the proportion of external air, in particular, for a high degree of humidity in the external air or the increase of service life of the air filters.

The ionization of the supply air and optionally additionally of the circulating air results advantageously particularly in the decomposition of gaseous volatile hydrocarbons, in the lowering of the oxidation potential of the air, and the elimination of microorganisms.

A method according to a further embodiment of the invention provides a natural feeling of comfort of the air in a room, wherein, in particular, gaseous volatile hydrocarbons are removed, the oxidation potential of the air is lowered, and microorganisms are eliminated.

According to a further embodiment of the invention, a minimum intensity of oxygen ions approximately equal to 5% of the installed ionization capacity of the air treatment device is ensured. This corresponds to the natural conditions.

The ionization power of the at least one ionization apparatus is controlled such according to a further embodiment of the invention that it increases with increasing proportions of volatile hydrocarbons and/or increase of the air velocity and/or increase of the relative air humidity and/or increased proportion of oxidizable air components. This ensures that an air supply, that is substantially not loaded, is introduced into the room or the recreation zone as a result of the predetermined air exchange and the optimized ionization intensity when the air quality in the room deteriorates.

A beneficial control of the ionization apparatus is advantageously possible according to further embodiments of the invention by means of a temporally supplied periodic alternating voltage. In this connection, the ionization apparatus is loaded with alternating pulses or alternating pulses combined to packages of a periodic alternating voltage that is available. The optimized discharge voltage is constant in this connection.

According to a further embodiment of the invention, the contents of ozone is lowered such that the desired in predetermined limit values of a comfortable room climate are ensured. In a first range, the power of the ionization apparatus is lowered. When the value of the ozone contents of the supply air increases despite the lowering of air ionization, at least one external ozone source is present. In this case, an operational mode for decomposition of ozone is switched on by means of the electronic control device. When the predetermined limits are again reached, the device is switched again to normal operation. In the operational mode "ozone decomposition", the energy level of the ozone is changed such that it decomposes. The fixed points for signalizing certain ozone values are selected such that a sufficient response safety is present.

The presence of at least one ozone sensor in the supply line and/or in the circulating line, wherein the at least one ozone sensor is connected to the control device and provides an electrical signal corresponding to the level of ozone or corresponding to the predetermined value or several predetermined values of the level of ozone, has the advantage that ozone occurring in at least one room can be immediately measured. Switching delays do not result in ozone being supplied to the room. Ozone that occurs in the room originates particularly from external sources in the rooms such as printers or copiers. A special advantage results when placing an ozone sensor in the supply line which provides the possibility of detecting ozone which is taken in with the atmospheric air. Ozone in the atmospheric air results from external sources such as motor vehicles or other apparatus causing air pollution. The particular advantage resides in that this ozone can be decomposed. This is particularly important in connection with closed rooms. Of course, ozone which is formed by other means in the supply air can be decomposed also.

The ozone decomposition is carried out in the pauses between the alternating pulses, the alternating pulse rates and/or the packages of alternating pulses by means of compensation of the charges of the ionized air caused thereby, wherein the ozone is converted to natural oxygen clusters/charged oxygen molecules. The control device can control temporal switching of periodic alternating current in the form of alternating pulses, alternating pulse rates and/or packages of alternating pulses of preset numbers and, in this way, the electrical output supplied by the control device to the ionization apparatus is adjusted automatically as a function of the value of the first air quality sensor, the airflow sensor, the humidity sensor and/or the second air quality sensor. When a preset ozone level is present, the momentary ionization output is reduced. When an increase of the ozone level occurs or the level of the ozone remains constant, the temporal spacing of the alternating pulses, of the alternating pulse rates, and/or of the packages of alternating pulses is changed wherein a compensation of the charges of the ionized air occurring in the pauses results in a conversion of ozone into natural oxygen clusters (charged oxygen molecules). The pauses are triggered in a targeted way by the control device for decomposing the ozone.

The presence of a continuous ionization intensity according to a further embodiment of the invention results in that the air supplied to the room is continuously affected. When sudden changes of the conditions occur, for example, by the presence of many smokers in the room or the presence of strongly acting cleaning supplies, the time constant before a reaction occurs is shortened substantially so that the room air is positively affected faster or is immediately neutralized.

DETAILED DESCRIPTION

A method and a device for air treatment of at least one room 9 by ionization and thus with ions will be explained in more detail in the following with one embodiment of the invention.

Figure 1:
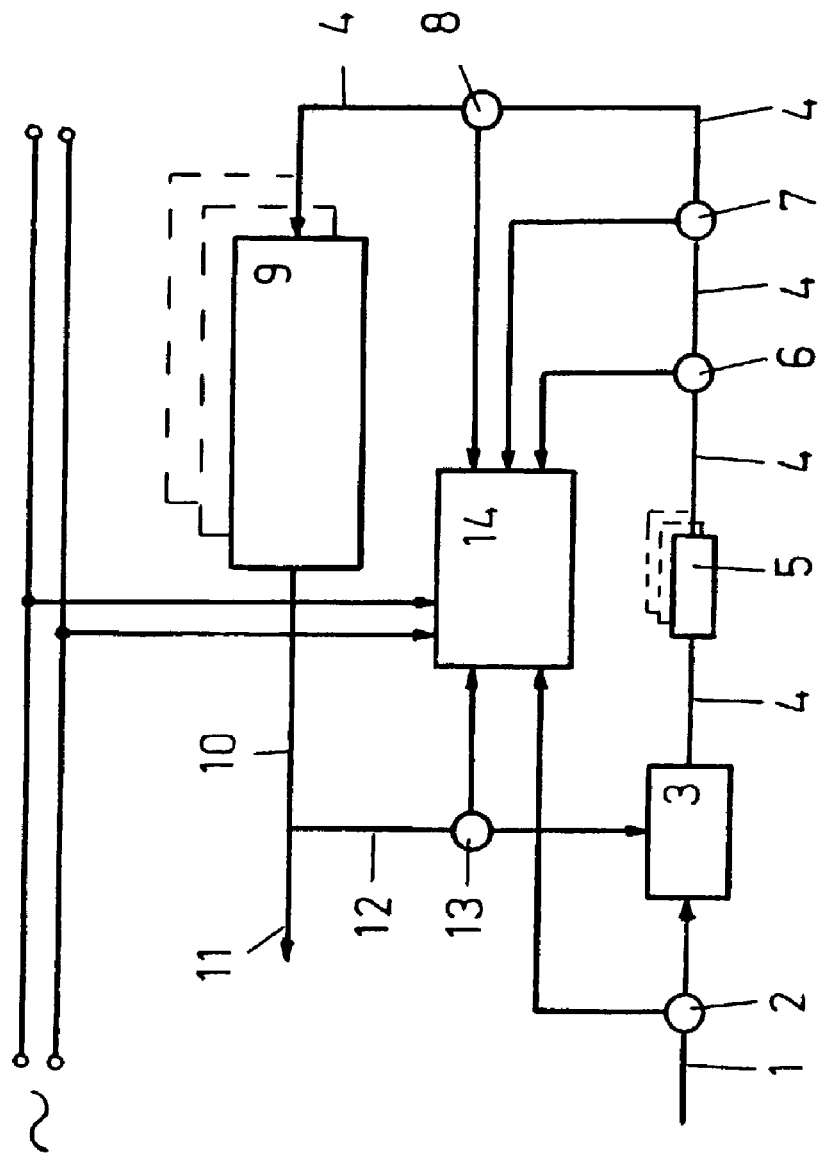
FIG. 1 shows a basic schematic illustration of the device for air treatment of at least one room by ionization.

FIG. 1 shows a basic schematic illustration of the device for air treatment of at least one room by air ionization. The object of the invention is to provide the room 9 with comfortable room air according to the specific requirements. Accordingly, a supply line 4 ends in this room 9.

The supply line 4 is connected to an air treatment device 3 to which is connected an external air intake 1 and the circulation line 12 coming from the room 9. The device comprises also an electronic control device 14 which is supplied with electrical power via electrical supply lines from an electrical power mains. This energy source is switched on when the air treatment device 3 is in operation wherein the supply ventilator conveys a supply flow of air.

The electronic control device 14 controls by means of a control line at least one ionization apparatus 5 which is positioned in the supply line 4 extending from the air treatment device 3 to the room 9. For this purpose, the electronic control device 14 receives information in the form of electrical signals from:

- a first air quality sensor 2 which considers the air quality of the external air flowing into the air treatment device 3, in particular, loading of the external air with volatile hydrocarbons (vaporous organic compounds—VOC) or with the actual oxidation potential of the external air,
- a second air-quality sensor 13 which is positioned in the circulation line 12 coming from the room 9 and guided to the air treatment device 3 or, optionally, in the exhaust line 10 or, optionally, in the room 9 and which also detects the volatile oxidizable air components of the room,
- an airflow sensor 6 which measures the flow velocity and thus the conveyed amount of air,
- an air humidity sensor 7, and
- an ozone sensor 8.

The airflow sensor 6, the air humidity sensor 7, and the ozone sensor 8 are positioned in the supply line 4 coming from the air treatment device 3 and guided into the room 9.

The air flow sensor 6 determines the flow velocity in the supply line 4 and the air humidity sensor 7 determines the relative humidity in the supply line 4.

Moreover, in the supply line 4 an ozone sensor 8 is positioned which determines ozone loading of the supply air and supplies electrical signals corresponding to this load value to the electronic control device 14.

The electrical power supplied to the ionization apparatus 5 by the electronic control device 14 is controlled as a function of the values of the first air quality sensor 2, the airflow sensor 6, the air humidity sensor 7, the ozone sensor 8, and/or the second air quality sensor 13. For this purpose, in the electronic control device 14 the signals of the first air quality sensor 2, the airflow sensor 6, the air humidity sensor 7, the ozone sensor 8, and the second air quality sensor 13 are combined with one another such that the electronic control device 14 provides a situation-specific power in the form of alternating pulse rates or several alternating pulse rates combined to packages or sets to the ionization apparatus 5 when a higher amount of air and/or a greater relative air humidity and/or a greater room air loading with VOC occurs. In this case, an increase of the alternating pulse rates or the number of alternating pulse rates combined to packages takes place. In a positive extreme situation, for example, when there is no loading of the room air, the ionization apparatus 5 is switched such that a minimal ionization intensity is provided anyway.

In the electronic control device 14 the following occurs:
- a weighting of the individual parameters and a combination as the sum of the individual vectors,
- a combination as a product of the individual amounts, or
- a different mathematical treatment so that the ionization apparatus is operated with a correspondingly optimized or desired power.

The ionization apparatus 5 is operated with temporal sequences of periodic alternating voltage of identical or approximately identical amplitude. The smallest unit of the sequence in this connection is a period of the periodic alternating voltage as an alternating pulse 15 (representation in FIG. 2). Unused periods of the periodic alternating voltage are removed. This ensures that the voltage remains constant during discharge and the functional data important for the process as a whole are stable as well as controllable. The periodic alternating voltage has in this connection a frequency which corresponds to the respective network frequency that is made available. A frequency converter is not required.

A stable air ionization and thus an optimized efficiency, i.e., a high proportion of positively and negatively loaded oxygen ions with a high bonding tendency, for example, with the VOC components in the air, and with a minimal proportion of radicals in the air, is generated only with the defined discharge voltage. The latter must be maintained substantially constant so that a minimal tolerance field is maintained.

Figure 2:
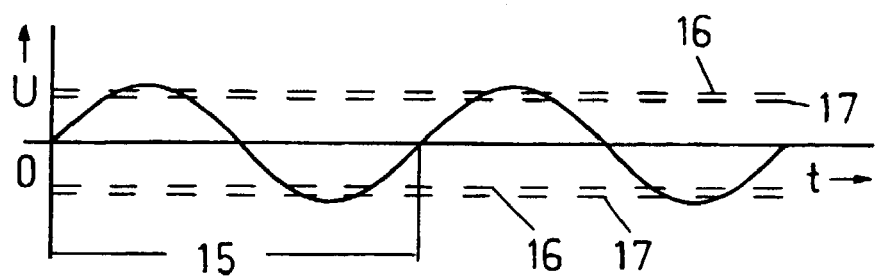
FIG. 2 is a basic illustration of a package of two alternating pulses for controlling the ionization apparatus.

In the following, the behavior of the corona discharge during changes of the discharge voltage upon surpassing the limit 16 and falling below the limit 17 of the tolerance field between the limits 16 and 17 of an optimal voltage for discharge is described in connection with the illustration of FIG. 2. When the limit 17 is surpassed by increasing the voltage of the ionization apparatus 5, the ozone loading in the supply air will increase progressively. When the discharge voltage falls below the limit 17, a working field of air ionization results which is characterized by a spontaneous corona discharge (buffer effect) wherein also undesirable oxygen radicals or ozone are released.

According to the invention, a defined discharge voltage in the process is maintained at a constant level. A situation-specific and stable air ionization is produced by a corresponding activation of the sine curve of the defined alternating voltage cut off upon passing through zero. In this connection, such a sine curve is a respective alternating pulse 15 which activates the ionization apparatus 5. For a further optimization of the function of the air ionization, the electronic control device 14 is designed such that additionally the alternating pulse rates are combined to meaningful packages or sets of certain numbers of alternating pulses 15.

The signals of the ozone sensor are processed as follows or used in the process as follows:

no action for an ozone proportion from 0 to 0.06 ppm in the supply air;

lowering of the current ionization power to 50% for ozone proportions greater/equal to 0.06 ppm;

upon further increase of the ozone proportion an external ozone sources is present, and the described measure for decomposition of ozone is started.

Decomposition of ozone is carried out in that simultaneously the spacing of the alternating pulses, of the alternating pulse rates, and/or the packages of alternating pulses is changed wherein the compensation of the charge of the ionized air taking place in the pauses results in a conversion of the ozone into natural oxygen clusters/charged oxygen molecules. The energy compensation corresponds substantially to that occurring in nature. Oxygen, charged oxygen, oxygen molecules, and ozone occur naturally in the atmosphere. Ozone is a labile component which upon energy take-up decomposes into charged bipolar oxygen molecules. This process is advantageously employed in the pauses for ozone decomposition.

The operation of the device according to the invention is carried out such that a minimum ionization power is maintained even when extremely low process data are present. This is, in particular, the case when the first air-quality sensor 2, the airflow sensor 6, the air humidity sensor 7, the ozone sensor 8, and the second air quality sensor 13 signal the electronic control device 14 that actually no ionization must be carried out. In this connection, the adequate natural effect is observed.

As a whole, the method and the device are provided for ensuring a natural comfort of room air.

During operation of the device only a minimal amount of exhaust air is returned via the exhaust line 11, and this amount corresponds to an amount of external air that is supplied via the external air supply line 1. This makes possible a directed use of the circulation air for the purpose of saving energy.

While specific embodiments of the invention have been shown and described in detail to illustrate the inventive principles, it will be understood that the invention may be embodied otherwise without departing from such principles.

What is claimed is:

1. A method for the treatment of air of at least one room by air ionization in an ionization apparatus comprised of electrical discharge ionization tubes or corona discharge tubes, the method comprising the steps of:

measuring values of:

oxidizable air components in the air to be treated;

relative humidity of the air to be treated;

flow velocity of the air to be treated or flow volume of the air to be treated;

ozone level in a supply air supplied to the at least one room; and intensity of oxygen ions; and determining a level of ionization power of the ionization apparatus based on the values measured by the means for measuring;

lowering, when a predetermined value of the ozone level is detected, the ionization power, and, when the ozone level continues to increase after the ionization power has been lowered indicating an external source of ozone, initiating a decomposition of ozone in the ionization apparatus by changing a time period of an applied periodic alternating voltage, supplied in the form of alternating pulses or packages of alternating pulses of a preset number or a combination of alternating pulses and packages of alternating pulses of a preset number.

2. The method according to claim 1, wherein, in the step of measuring, loading of external air with volatile hydrocarbons is measured with a first air-quality sensor; the flow velocity or the volume flow of the air to be treated is measured with an airflow sensor; the relative air humidity of the air to be treated is measured with an air humidity sensor; an ozone level in at least one of the supply air and the air to be treated is measured with an ozone sensor; and the oxidizable air components of the air of the at least one room, of exhaust air of the room in an exhaust line, and of the circulating air in a circulation line, extending between the exhaust line and an air treatment device, is measured with a second air-quality sensor; and further comprising the step of controlling, based on the measured parameters, the level of ionization power of the at least one ionization apparatus such that an intensity of oxygen ions is reduced and, when too high an ozone level is present, the ozone level is lowered by decomposition.

3. The method according to claim 2, further comprising the step of ensuring the intensity of oxygen ions to be approximately 5% of an ionization capacity of the ionization apparatus.

4. The method according to claim 2, wherein, in the step of determining, the ionization power is increased by logic combination of the measured parameters when at least one of a proportion of volatile hydrocarbons in the external air, the air velocity, the relative air humidity, and oxidizable air components increases.

5. The method according to claim 1, further comprising the step of controlling the at least one ionization apparatus by a temporally applied periodic alternating voltage, supplied in the form of at least one of at least one alternating pulse and at least one package of alternating pulses of a preset sequence.

6. The method according to claim 5, wherein for an ozone level in a supply line of at least 0.06 ppm the ionization power is lowered and for a further increase of the ozone level in the supply line a time period of the applied periodic alternating voltage is changed such that in the ionization apparatus decomposition of ozone is initiated.

7. The method according to claim 1, wherein an ionization intensity is present for low process data not causing any control action.

* * * * *